| United States Patent [19] | [11] | 4,447,607 |
| Johnson | [45] | May 8, 1984 |

[54] DIBENZO DIAZACINES

[75] Inventor: Roy A. Johnson, Brookline, Mass.

[73] Assignee: The Upjohn Company, Kalamazoo, Mich.

[21] Appl. No.: 439,481

[22] Filed: Nov. 5, 1982

[51] Int. Cl.³ .......................................... C07D 239/70
[52] U.S. Cl. ................................ 544/246; 260/244.4; 260/245.6
[58] Field of Search ..................... 544/246; 260/244.4, 260/245.6

[56] References Cited

U.S. PATENT DOCUMENTS 4,112,224  9/1978  Bundy ................................. 542/426

FOREIGN PATENT DOCUMENTS 2039903A  12/1979  United Kingdom .

OTHER PUBLICATIONS

D. Harris, et al., Advances in Prostaglandin and Thromboxane Research, 6:437 (1980).
T. Miyomoto, et al., Advances in Prostaglandin and Thromboxane Research 6:443 (1980).
H. Tai, et al., Advances in Prostaglandin and Thromboxane Research, 6:447 (1980).
Copending application Ser. No. 430,306; filed Sep. 30 1982, R. A. Johnson.
Copending application Ser. No. 430,305; filed Sep. 30 1982, R. A. Johnson.
Copending application Ser. No. 430,293; filed Sep. 30 1982, R. A. Johnson.
Copending application Ser. No. 430,294; filed Sep. 30 1982, R. A. Johnson.

*Primary Examiner*—Jane T. Fan
*Attorney, Agent, or Firm*—Lawrence T. Welch

[57] ABSTRACT

The present invention provides novel dibenzo diazocines which are useful as thromboxane $A_2$ ($TXA_2$) synthetase inhibitors and as such represent potent pharmacological agents.

7 Claims, No Drawings

DIBENZO DIAZACINES

DESCRIPTION

1. Background of the Invention

The present invention relates to novel compositions of matter. More particularly, the present invention relates to dibenzo diazocines and derivatives thereof. These compounds are potent thromboxane $A_2$ inhibitors and as such represent useful pharmacological agents.

Since the discovery that human platelets convert the prostaglandin endoperoxide ($PGH_2$) into a labile proaggregatory molecule known as thromboxane $A_2$ ($TXA_2$), researchers have sought compounds that could selectively inhibit the biological activity of $TXA_2$. This end may be achieved in two different ways: the synthesis of $TXA_2$ can be blocked by inhibiting the $TXA_2$ synthetase, or a compound could be a receptor level antagonist of $TXA_2$. As therapeutic agents, $TXA_2$ synthetase inhibitors are more useful. See, e.g., R. Gorman, "Biological and Pharmacological Evaluation of Thomboxane Synthetase Inhibitors," Advances in Prostaglandin and Thromboxane Research, 6:417 (1980), and references cited therein. Most important are compounds which selectively inhibit $TXA_2$ synthetase. Id.

2. Prior Art

A number of $TXA_2$ synthetase inhibitors are known. See for example the bi-heterocyclic 9,11-trideoxy-PGF-type compounds disclosed in U.S. Pat. No. 4,112,224; SQ 80,388 [1-(3-phenyl-2-propenyl)-1H-imidazole] disclosed in D. Harris, et al., Advances in Prostaglandin and Thromboxane Research 6:437 (1980); pyridine and its derivatives, disclosed in T. Miyamoto, et al., Advances in Prostaglandin and Thromboxane Research, 6:443 (1980), and British patent application No. 2,039,903A (abstracted in Derwent Farmdoc No. 50111C (1980)). See also H. Tai, et al., Advances in Prostaglandin and Thromboxane Research, 6:447 (1980). Other compounds which have been disclosed as thromboxane synthetase inhibitors, include sodium p-benzyl-4(1-oxo-2-(4-chlorobenzyl)-3-phenylpropyl)-phenyl phosphate, imidazoles, nordihydroguaiaretic acid, and 12L-hydroperoxy-5,8,10,14-eicosatetraenoic acid (HETE). As noted in the above named British patent specification, however, the inhibitory activity of these latter compounds on thromboxane synthetase is very weak making them unsatisfactory as practically effective medicines.

Copending applications Ser. Nos. 430,306; 430,305; 430,293; and 430,294, all filed on Sept. 30, 1982 disclose pyridyl-substituted benzofurans as $TXA_2$ synthetase inhibitors.

SUMMARY OF THE INVENTION

Surprisingly and unexpectedly it has been found that selective thromboxane synthetase inhibition may be achieved by employing a compound of the formula I or II, or a pharmaceutically acceptable acid addition salt thereof,
wherein $Z_1$ is
 (a) 3- or 4-pyridyl or
 (b) 1-imidazolyl;
wherein $R_1$ and $R_2$ are the same or different and are
 (a) hydrogen,
 (b) ($C_1$–$C_4$)alkyl,
 (c) phenyl,
 (d) phenyl mono-, di-, or tri-substituted by
  (i) ($C_1$–$C_4$)alkyl,
  (ii) a halogen atom,
  (iii) hydroxyl,
  (iv) amino
  (v) an amine of the formula, —$NR_3R_4$, wherein $R_3$ and $R_4$ are the same or different and are hydrogen or ($C_1$–$C_4$)alkyl,
  (vi) cyano,
  (vii) hydroxy-carbonyl
  (viii) ($C_1$–$C_4$)alkoxy carbonyl,
  (ix) nitro, or
  (x) ($C_1$–$C_4$)alkoxy,
 (e) ($C_7$–$C_{12}$)aralkyl, or
 (f) a 5 or 6 membered heteroaromatic ring, with the heteroatoms being nitrogen, sulfur, or oxygen, the remainder being carbon.

The carbon atom content of various hydrocarbon-containing moieties is indicated by a prefix designating the minimum and maximum number of carbon atoms in the moiety, i.e., the prefix ($C_i$–$C_j$) indicates a moiety of the integer "i" to the integer "j" carbon atoms, inclusive. Thus ($C_1$–$C_3$)alkyl refers to alkyl of one to 3 carbon atoms, inclusive, or methyl, ethyl, propyl, and isopropyl.

Examples of alkyl of one to 4 carbon atoms, inclusive, are methyl, ethyl, propyl, butyl, and isomeric forms thereof.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by halo or alkyl of one to 3 carbon atoms, inclusive, are p-chlorophenyl, m-bromophenyl, 2,4-difluorophenyl, 2,4,6-trichlorophenyl, p-tolyl, m-tolyl, o-tolyl, p-ethylphenyl, 2,5-dimethylphenyl, 4-chloro-2-methylphenyl, and 2,4-dichloro-3-methylphenyl.

Examples of heteroaromatic-rings within the scope of $R_1$ and $R_2$ include pyridinyl, imidazolyl, furan, thiophenyl, pyrimidyl, and the like. Preferred among these substituents are 3-pyridyl, or 1-imidazolyl. Pharmaceutically acceptable acid addition salts are formed at the heterocyclic amine moiety and are also useful for administering the compounds of this invention. These salts include hydrochloride, hydrobromide, hydroiodide, sulfate, phosphate, acetate, propionate, lactate, maleate, malate, succinate, tartrate, and the like. They are prepared by methods well known in the art.

The compounds of the present invention will be named herein as dibenzo diazocines using the Chemical Abstracts numbering system (see Naming and Indexing of Chemical Substances for Chemical Abstracts during the Ninth Collective Period (1972–1976), a reprint of section IV from the Volume 76 Index Guide.)

The compounds of the present invention were tested for $TXA_2$ inhibition as follows:

Rabbit aortic strips were superfused in series with Krebs solution. Thromboxane $A_2$ ($TXA_2$) was generated by mixing prostaglandin $H_2$ ($PGH_2$) with human platelet microsomes (HPM).

Potential inhibitors were tested by comparing the response of the rabbit aorta to the amount of $TXA_2$ produced by mixing $PGH_2$ and HPM without the test compound in the reaction medium and then the amount of $TXA_2$ produced when the test compound was added to the HPM 5 minutes before the HPM was mixed with $PGH_2$. By this means compounds which selectively inhibit $TXA_2$ synthetase are found. For a discussion of TXA$_2$ synthetase inhibition testing see, e.g., R. Gorman, supra.

Using this test system, one compound, 2,8-di(3-pyridyl)methyl-6H,12H-5,11-methanodibenzo[b,f][1,5-]diazocine (Example 1) has been shown to be the most effective in inhibiting TXA$_2$ formation. This compound has an approximate ED$_{50}$ in this system of between 10 and 100 ng/ml.

The novel compounds of this invention have thus been shown to be highly active as selective inhibitors of the thromboxane synthetase enzyme system. Accordingly, these novel compounds are useful for administration to mammals, including humans, whenever it is desirable medically to inhibit this enzyme system. For a discussion of the utility of TXA$_2$ inhibitors, see, e.g., Derwent Farmdoc Nos. 18399B; 72896B; 72897B; 63409B; 03755C; 03768C; and 50111C.

Thus, for example, these novel compounds are useful as antiinflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 100 μg per kg per minute until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

These compounds are useful whenever it is desired to inhibit platelet aggregation, reduce the adhesive character of platelets, and remove or prevent the formation of thrombi in mammals, including man, rabbits, dogs, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of these at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

The compounds of the present invention are useful in mammals, including humans and certain useful animals, e.g., dogs and pigs, to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 μg to about 500 μg/kg of body weight per minute, or in a total daily dose by injection or infusion in the range about 0.1 to about 20 mg/kg of body weight per day, the exact dose depending on the age, weight, and condition of the patient or animal, and on the frequency and route of administration.

Thromboxane synthetase converts PGH$_2$ (prostaglandin endoperoxide) into TXA$_2$. PGH$_2$ is also converted to prostacyclin, PGD$_2$, and other compounds by other enzymes. Thus, because the compounds of this invention inhibit thromboxane A$_2$ synthetase, they increase the PGH$_2$ substrate and thus increase the amount of endogenous prostacyclin. Therefore, they are also useful for many of the pharmacological purposes for which prostacyclin is employed.

Prostacyclin and a thromboxane synthetase inhibitor have both been shown to be effective in controlling tumor cell metastasis, see, e.g., K. Honn, et al., "Thromboxane Synthetase Inhibitors and Prostacyclin Can Control Tumor Cell Metastasis," an Abstract of the Twentieth Annual Meeting of the American Society for Cell Biology, in the Journal of Cell Biology, 87:64 (1980).

Similarly, prostacyclin has been shown to be an effective antihypertensive agent. The compounds of the present invention are also used for this purpose. (See, e.g., British patent specification No. 2,039,903A).

For a general discussion of the utility of TXA$_2$ synthetase inhibitors which increase endogenous prostacyclin, see, Aiken, et al. J. Pharmacol. Exp. Ther., 219:299 (1981).

The compounds of the present invention are prepared by the method depicted in Chart A. An amino-phenyl-pyridine or amino-phenyl-imidazole of the Formula A-1 (3-(4-aminophenyl)pyridine and 4-(3-aminophenyl)pyridine are well known, readily available compounds or are prepared as described in copending application Ser. No. 430,306 filed Sept. 30, 1982; the corresponding imidazole is disclosed, e.g., in Baggaley, et al., J. Med. Chem. 18:833–836 (1975)) is treated with hexamethylenetetramine in trifluoroacetic acid to yield 2,8-di(3-pyridyl)methyl-6H,12H-5,11-methanodibenzo[b,f][1,5-]diazocine of the formula A-2. Treatment of this compound with nitrous acid yields the bis-N-nitroso compound of the formula A-3. Reduction of this compound by treatment with cuprous chloride in acetic acid yields the di-sec-amine of the formula A-4. This compound A-4 compound is a key intermediate to prepare the compounds of the present invention. These compounds are prepared by reacting the formula A-9 compound with an appropriate aldehyde or ketone of the formula $R_1$—CO—$R_2$ wherein $R_1$ and $R_2$ are as defined above.

Certain compounds of the present invention are preferred. Thus, compounds of the formula II, wherein $Z_1$ is 3-pyridyl and wherein $R_1$ and $R_2$ are hydrogen, methyl, phenyl, 1-imidazolyl, or 3-pyridyl are preferred. Compounds of this latter class wherein $R_1$ and $R_2$ are hydrogen are more preferred. Thus, 2,8-di(3-pyridyl)methyl-6H,12H-5,11-methanodibenzo[b,f][1,5-]diazocine is the most preferred compound of this invention.

DESCRIPTION OF THE PREFERRED EMBODIMENTS

The operation of the present invention is seen more fully by the examples given below.

EXAMPLE 1

2,8-Di(3-pyridyl)-6H,12H-5,11-methanodibenzo[b,f][1,5]diazocine (Formula II, $R_1$ and $R_2$ are hydrogen)

Refer to Chart A (conversion of A-1 to A-2).

A solution of 3-(4-aminophenyl)pyridine (0.980 g., 0.00575 mole) and hexamethylenetetramine (0.807 g., 0.00575 mole) in trifluoroacetic acid (18 ml) is stirred at room temperature. TLC (thin-layer chromatography-acetone) analyses after 20 hr and 92 hr are similar and indicate formation of two more polar materials. The excess trifluoroacetic acid is removed under reduced presure and water (25 ml) is added to the residue. The aqueous solution is made alkaline with solid sodium carbonate and is extracted twice with ethyl acetate and twice with methylene chloride. The separate extracts are dried over magnesium sulfate, filtered, and concentrated. From the ethyl acetate extract there is obtained a crude yield of 0.810 g of oil and from meylene chloride there is obtained 0.301 g of oil. Addition of acetone to each results in formation of crystals. These are collected together by filtration and give 0.160 g of crystals with a m.p. of 175°–225° C., whose TLC mobility is the same as the more polar of the two components seen in the reaction mixture.

The combined filtrates from the crystals are chromatographed over one Merck size B Lobar silica gel column using acetone as the solvent and collecting 25 ml fractions. The less polar material elutes in fractions 32–42 and after pooling and crystallization from acetone-hexane gives a first crop (0.245 g) and a second crop (0.028 g) of desired product. The more polar product elutes in fractions 73–96 and gives, after crystallization from acetone, 0.072 g of material.

Two recrystallizations of the less polar product from acetone-hexane give colorless crystals, with a m.p. of 188°–190° C.; infrared (Nujol) peaks of 1609, 1590, 1574, 1500, 1436, 1361, 1347, 1318, 1301, 1209, 1170, 1158, 1118, 1104, 1071, 1018, 968, 961, 954, 942, 889, 884, 866, 849, 837, 815, 808, 801, 749, 722, 715, and 650 $cm^{-1}$; $^1H$ NMR (CDCl$_3$, δ) reveals peaks at 8.77, 8.55, 7.77, 7.10–7.50, 4.84, 4.38, and 4.26. The mass spectrum yields ions at m/e 376.1688 and 374. No other signals are stronger than 10%.

Anal. Calcd. for $C_{25}H_{30}N_4$: C, 79.76; H, 5.36; N, 14.88. Found: C, 78.98, 78.41; H, 5.48, 5.52; N, 14.73, 14.71.

PREPARATION 1

2,8-Di(3-pyridyl)methyl-5,11-dinitroso-5,6,11,12-tetrahydrodibenzo[b,f][1,5]diazocine Refer to Chart A (conversion of A-2 to A-3).

A solution of the compound of Example 1 (4.042 g, 0.010 mole) in concentration HCl (60 ml) is placed in a 500 ml 3-necked round-bottom flask and is stirred and cooled in an ice bath. A solution of sodium nitrite (8.8 g, 0.127 mole) in water (50 ml) is added via a dropping funnel over a period of an hour. The solution becomes orange in color and a crystalline solid precipitates. The reaction mixture is poured into ice and made alkaline by the careful addition of 50% aqueous sodium hydroxide. Unchanged solid is collected and reworked with aqueous base. Both aqueous mixtures (original and reworked) are extracted with methylene chloride, the extracts are combined and dried over magnesium sulfate, filtered, and concentrated. The solid residue is taken up in methylene chloride, treated with activated charcoal, filtered, and then crystallized from methylene chloride-hexane. A first crop (3.309 g., 0.00735 mole, 73%) of crystals with a m.p. 200°–202° C., is obtained. The compound is used directly in the next step.

EXAMPLE 2

2,8-Di(3-pyridyl)methyl-5,6,11,12-tetrahydrodibenzo[b,f][1,5]diazocine (Formula I)

Refer to Chart A (conversion of A-3 to A-4).

A solution of the compound of preparation 1 (3.309 g, 0.00735 mole) in glacial acetic acid (50 ml) is placed in a 250 ml Erlenmeyer flask. To this is added a solution of cuprous chloride (2.20 g, 0.022 mole) in concentrated aqueous hydrochloric acid (12 ml). A dark, thick precipitate forms. The mixture is warmed on a steam bath. Additional concentrated hydrochloric acid is added and the mixture is warmed 10 minutes longer. TLC (10% methanol in chloroform) of a sample of the reaction quenched in aqueous sodium carbonate-ethyl acetate shows about a 1:1 ratio of starting material to product. The mixture is heated an additional 15 min with no change by TLC. Additional cuprous chloride (2.2 g) in concentrated hydrochloric acid (10 ml) is added and some foaming of the mixture is seen. The mixture is heated 10 minutes after which TLC shows the starting material to be essentially all converted to a new product. The reaction is poured onto ice and the aqueous mixture is made alkaline by the careful addition of aqueous sodium hydroxide. Extraction with methylene chloride is difficult as a fine precipitate is present and the mixture also forms an emulsion. The mixture is finally filtered through Celite. The organic layer of the filtrate is separated and the Celite and solids as well as the aqueous portion of the filtrate are further extracted with ethyl acetate. The extracts are dried over magnesium sulfate, filtered, and concentrated separately. From the methylene chloride-hexane, 1.363 g of crystals with a m.p. of 197°–207° C. are obtained. The sample is dissolved in hot methanol, treated with activated charcoal, and crystallized from a reduced volume of methanol. Colorless titled crystals with a m.p. of 228°–229° C. are obtained; infrared (Nujol) peaks are observed at 3254, 3208, 3178, 161, 1591, 1575, 1530, 1506, 1478, 1434, 1432, 1318, 1300, 1276, 1262, 1232, 1186, 1049, 1029, 845, 810, 710, and 632 $cm^{-1}$.

Anal. Calcd. for C$_{26}$H$_{24}$N$_4$: C, 79.56; H, 6.16; N, 14.28. Found: C, 78.45, 78.99; H, 6.25, 6.18; N, 14.11, 14.09.

EXAMPLE 3

2,8-Di(3-pyridyl)methyl-13,13-dimethyl-6H,12H-5,11-methanodibenzo[b,f][1,5]diazocine (Formula II, R$_1$, R$_2$ are methyl)

Refer to Chart A (conversion of A-4 to A-5).

A solution of the compound of Example 2 (0.196 g, 0.00050 mole) in acetone (50 ml) is heated to reflux temperature for 6 hrs. The solvent is removed under reduced pressure leaving a gummy residue (0.206 g). The residue is chromatographed over silica gel (10 g) packed as a slurry in acetone. Fractions of 25 ml volume are collected and the product (0.187 g) is eluted in fractions 6-19. $^1$H NMR ($\delta$, CDCl$_3$) yields peaks at 8.44, 740, 6.52-7.23, 4.65, 4.06, 3.78, and 1.39. The mass spectrum reveals ions at 432.2322, 417, 389, and 235 m/e.

EXAMPLE 4

2,8-Di(3-pyridyl)methyl-13-phenyl-6H,12H-5,11-methanodibenzo[b,f][1,5]diazocine (Formula II, R$_1$ is phenyl, R$_2$ is hydrogen)

Refer to Chart A (conversion of A-4 to A-5).

A mixture of the compound of Example 3 (0.196 g, 0.00050 mole) and benzaldehyde (0.061 g, 0.000575 mole) in toluene (50 ml) is heated to reflux temperature in an apparatus fitted with a Dean-Stark trap. The solution is refluxed 45 minutes and then left at room temperature for a week. Crystals (0.121 g) in the solution are collected and are shown by their infrared spectrum to be the starting compound. TLC (acetone) of the solution shows formation of a new material whose NMR spectrum is consistent with the expected product. Evaporation of the solution leaves 0.066 g of viscous gum. The unreacted crystals and benzaldehyde (0.079 g) are heated to reflux temperature in toluene for 5 hours, after which reaction is complete. The solvent is removed under reduced pressure and the residue is dissolved in 0.1 N hydrochloric acid and washed twice with ether. The aqueous layer is made alkaline with 1 N sodium hydroxide and extracted three times with ether. The ether extracts are pooled, washed with brine, dried over magnesium sulfate, filtered, and concentrated. The crude product (0.140 g) is combined with the 0.066 g of material isolated above and chromatographed over a Merck size A Lobar silica gel column, using acetone as the solvent. Fractions (10 ml) 7-11 contain 0.156 g of the desired titled product. $^1$H NMR (CDCl$_3$, $\delta$) yields peaks at 6.90-7.70, 6.77, 6.43, 5.30, 4.80, 4.28, 4.16, 3.82, and 3.70. The mass spectrum yields ions at 480.2311, 389, 297, and 284 m/e.

EXAMPLE 5

2,8-Di(3-pyridyl)methyl-13-(3-pyridyl)-6H,12H-5,11-methanodibenzo[b,f][1,5]diazocine (Formula II, R$_1$ is 3-pryidyl, R$_2$ is hydrogen)

Refer to Chart A (conversion of A-4 to A-5).

A mixture of the compound of Example 4 (0.196 g, 0.00050 mole) and pyridine-3-carboxaldehyde (0.072 g, 0.00067 mole) in toluene (50 ml) is heated to reflux temperature with the condensate being passed through a Dean-Stark trap. The reaction is heated to reflux for 16 hours after which the starting material has been consumed. Solvent is removed under reduced pressure and the residue is chromatographed over a Merck size A Lobar silica gel column using acetone as the solvent. The pure product 0.184 g is obtained in fractions (10 ml each) 9-16 and is a viscous gum. $^1$H NMR (CDCl$_3$, $\delta$) reveals peaks at 8.88, 8.47, 7.90, 6.93-7.56, 6.82, 6.50, 5.33, 4.82, 4.31, 4.13, 3.92, 3.88, and 3.76.

FORMULAS

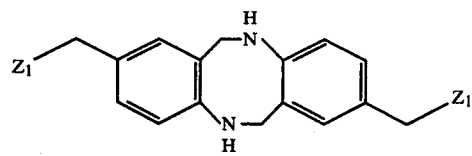

I

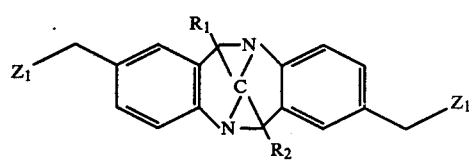

II

CHART A

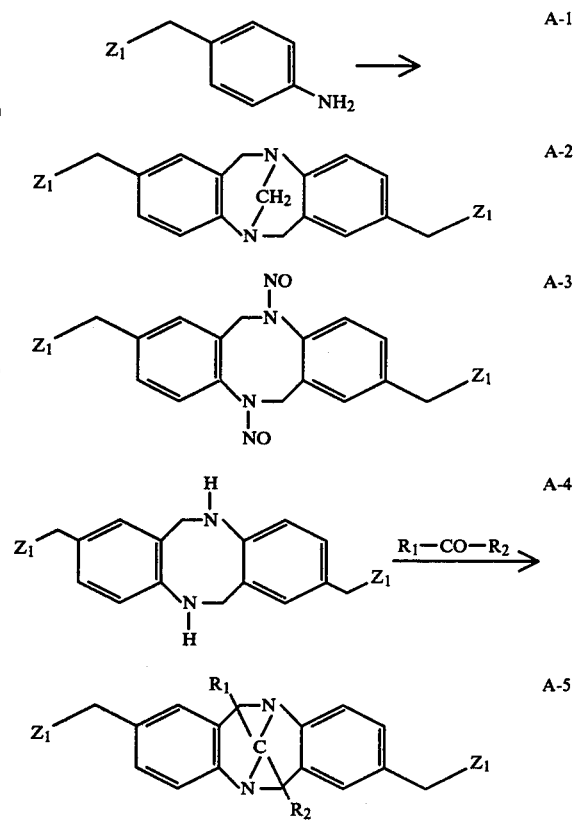

I claim:
1. A compound of the formula I or II

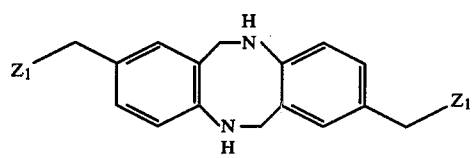

I

-continued

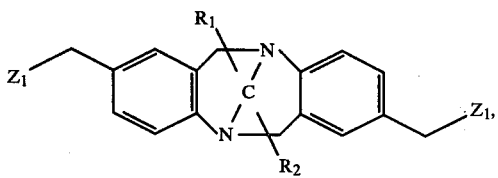
II or a pharmaceutically acceptable acid addition salt thereof, wherein $Z_1$ is
 (a) 3- or 4-pyridyl, or
 (b) 1-imidazolyl;

wherein $R_1$ and $R_2$ are the same or different and are
 (a) hydrogen,
 (b) $(C_1-C_4)$alkyl,
 (c) phenyl,
 (d) phenyl mono-, di-, or tri-substituted by
  (i) $(C_1-C_4)$alkyl,
  (ii) a halogen atom,
  (iii) hydroxyl,
  (iv) amino
  (v) an amine of the formula, $-NR_3R_4$, wherein $R_3$ and $R_4$ are the same or different and are hydrogen or $(C_1-C_4)$alkyl,
  (vi) cyano,
  (vii) hydroxy-carbonyl
  (viii) $(C_1-C_4)$alkoxy carbonyl,
  (ix) nitro, or
  (x) $(C_1-C_4)$alkoxy,
 (e) $(C_7-C_{12})$aralkyl, or
 (f) 3-pyridyl or 1-imidazolyl.

2. A compound of claim 1, wherein $R_1$ and $R_2$ are the same or different and are hydrogen, methyl, phenyl, or 3-pyridyl and $Z_1$ is 3-pyridyl.

3. 2,8-Di(3-pyridyl)methyl-5,6,11,12-tetrahydrodibenzo[b,f][1,5]diazocine, a compound of claim 1.

4. 2,8-Di(3-pyridyl)methyl-6H,12H-5,11-methanodibenzo[b,f][1,5]diazocine, a compound of claim 2.

5. 2,8-Di(3-pyridyl)methyl-13,13-dimethyl-6H,12H-5,11-methanodibenzo[b,f][1,5]diazocine, a compound of claim 2.

6. 2,8-Di(3-pyridyl)methyl-13-phenyl-6H,12H-5,11-methanodibenzo[b,f][1,5]diazocine, a compound of claim 2.

7. 2,8-Di(3-pyridyl)methyl-13-(3-pyridyl)-6H,12H-5,11-methanodibenzo[b,f][1,5]diazocine, a compound of claim 2.

* * * * *